US005777099A

United States Patent [19]
Mehra

[11] Patent Number: 5,777,099
[45] Date of Patent: Jul. 7, 1998

[54] RNA SEPARATION

[75] Inventor: Manmohan Mehra, Friendswood, Tex.

[73] Assignee: Biotecx Laboratories, Inc., Houston, Tex.

[21] Appl. No.: 706,260

[22] Filed: Sep. 4, 1996

Related U.S. Application Data

[63] Continuation-in-part of Ser. No. 393,668, Feb. 24, 1995, abandoned.

[51] Int. Cl.$^6$ ................................................. C07H 21/02
[52] U.S. Cl. ................... 536/25.42; 536/25.1; 536/25.4; 536/25.41
[58] Field of Search ................................ 536/25.1, 25.4, 536/25.41, 25.42

[56] References Cited

U.S. PATENT DOCUMENTS

| | | | |
|---|---|---|---|
| 3,389,133 | 6/1968 | Gutcho | 536/25.4 |
| 4,830,969 | 5/1989 | Holmes | 435/259 |
| 4,843,155 | 6/1989 | Chomczynski | 536/25.41 |
| 5,130,423 | 7/1992 | Van Ness et al. | 536/25.41 |
| 5,234,809 | 8/1993 | Boom et al. | 435/91 |
| 5,300,635 | 4/1994 | Macfarlane | 536/25.4 |
| 5,346,994 | 9/1994 | Chomczynski | 530/419 |
| 5,393,672 | 2/1995 | Van Ness et al. | 436/94 |
| 5,422,241 | 6/1995 | Goldrick et al. | 435/6 |

FOREIGN PATENT DOCUMENTS

| | | |
|---|---|---|
| 0554034 | 8/1993 | European Pat. Off. |
| 2040615 | 10/1993 | Spain |

OTHER PUBLICATIONS

Chomczynski, "A Reagent for the Single–Step Simultaneous Isolation of RNA, DNA and Protein from Cells and Tissue Samples," *Biotechniques*, 15(3), 532–537 (1993).

Chomczynski et al., "Single–Step Method of RNA Isolation by Acid Guanidinium Thiocyanate–Phenol–Chloroform Extraction," *Analytical Biochemistry*, 162(1), 156–159 (1987).

Siebert et al., "Modified Acid Guanidinium Thiocyanate–Phenol–Chloroform RNA Extraction Method Which Greatly Reduced DNA Contamination," *Nucleic Acids Research*, 21(8), 2019–2020 (1993).

R. A. Cox, "The Use of Guanidinium Chloride in the Isolation of Nucleic Acids," Ch. 103a in *Method in Enzymology, vol. XII, Nucleic Acids, Part B*, Grossman et al. eds., Academic Press, New York, NY, 1968, pp. 102–129.

Biotecx Bulletin No. 27, "Ultraspec RNA Isolation System," Biotecx Laboratories, Houston, TX, Feb., 1993.

Biotecx Bulletin No. 28, "Ultraspec–II RNA Isolation System," Biotecx Laboratories, Houston, TX, Oct., 1993.

Chirgwin et al., "Isolation of Biologically Active Ribonucleic Acid From Sources Enriched in Ribonuclease," *Biochemistry*, 18(24), 5294–5299 (1979).

*Stedman's Medical Dictionary*, 25th Ed., Williams and Wilkins, Baltimore, MD, 1990, see p. 283, col. 2.

*Primary Examiner*—John Kight
*Assistant Examiner*—L. Eric Crane
*Attorney, Agent, or Firm*—Bush, Riddle & Jackson

[57] ABSTRACT

An improved process for the separation of RNA from a liquid sample of biological origin containing RNA comprises (a) intimately contacting the sample with a two-phase composition wherein the upper phase is predominately phenol and the lower phase is an aqueous solution comprising at least one water-soluble guanidinium salt, a buffer and urea, the water content of the aqueous phase being relatively low, (b) adding a relatively dense water-insoluble solvent and (c) recovering RNA from the resulting aqueous phase.

15 Claims, No Drawings

RNA SEPARATION

RELATION TO EARLIER FILED APPLICATION

This application is a continuation-in-part of U.S. patent application Ser. No. 08/393,668 filed Feb. 24, 1995, now abandoned.

FIELD OF THE INVENTION

This invention relates to a process of separating RNA from other materials of biological origin and to a two-phase composition employed in such a process.

BACKGROUND OF THE INVENTION

Many current studies in the molecular biology field require ribonucleic acid (RNA) in a relatively pure form. In biological materials, RNA is often found in conjunction with deoxyribonucleic acid (DNA), proteins and other substances. In particular, for studies involving genes, the RNA must be separated from the DNA and other substances with which it is found.

U.S. Pat. No. 4,830,969 to David Holmes discloses a procedure for the separation of RNA from solid cellular materials by use of a solution containing urea or guanidine hydrochloride, surfactants and optionally a buffer.

U.S. Pat. No. 5,300,635 to Donald Macfarlane describes a method of isolating RNA from liquid samples using selected quaternary amine surfactants.

Cox, Methods in Enzyonolgy, 12(B): 120–9 (1968), describes a method for RNA separation using guanidinium chloride. This procedure appears to be lengthy and produces RNA which needs repurification.

A possibly better method is described by Chirgwin et al., Biochem 18: 5294–9 (1979). In this procedure, an RNA-containing solid tissue is homogenized in a solution containing guanidinium thiocyanate, sodium acetate and beta-mercaptoethanol at pH 7. The homogenate is recovered, acidified and mixed with ethanol to precipitate the RNA which is then purified. This process is also time-consuming, taking up to two days.

A more rapid method for RNA isolation is described in U.S. Pat. No. 4,843,155 of Chomczynski. This method uses a reagent comprising a solution of guanidinium chloride or guanidinium thiocyanate, phenol and a buffer. Although multi-phase mixtures are encountered during separation procedures, the reagant of Chomczynski is a solution, i.e. a homogeneous mixture having a single phase. The disclosed method is said to produce RNA, after purification, in a substantially pure and undegraded form. To obtain the one-phase solution, the phenol content must be relatively high, e.g., as high as about 50% by volume. Solutions containing this percentage of phenol are considered hazardous by the U.S. Department of Transportation and are subject to restrictions in labeling and shipping. The water content of the solutions of U.S. Pat. No. 4,843,155, if any, is not specified.

More recently, related compositions containing a lesser proportion of phenol, and thus not subject to D.O.T. restrictions, have become commercially available. Such compositions contain from about 30% to about 40% by volume of phenol. As a result of the lower phenol content, such compositions are two-phase heterogeneous mixtures wherein the upper phase is predominately phenol and the lower phase is an aqueous solution of guanidinium thiocyanate and/or guanidinium chloride, urea, a buffer and other components. These two-phase solutions are illustrated by ULTRASPEC® RNA Isolation System and ULTRASPEC®-II RNA Isolation System and have been commercial since 1992 and 1993, respectively, being marketed by BIOTECX.

In the case of Ultraspec RNA Isolation System, the two-phase composition is shaken and homogenized with biological tissue. Chloroform is added to the homogenate with two phases resulting. The upper aqueous phase is separated and treated with ethanol or isopropanol to precipitate the RNA. The supernatant liquid is removed and the RNA is washed and partially dried. The Ultraspec-II RNA Isolation System is employed in a similar manner except that, after the addition of chloroform, an amount of isopropanol insufficient to precipitate the RNA is added. The RNA is separated by the addition of RNA Tack® Resin, a silica-containing resin. The RNA is then recovered by elution of the resulting pellet.

These methods are useful for the separation of RNA from biological tissue, cells such as eukaryotic/prokaryotic cells, and blood or other biological materials. The above Ultraspec methods are particularly useful when the biological sample is solid but somewhat poorer results are obtained when they are employed to separate RNA from liquid samples. It would be of advantage to provide a composition, not subject to labeling and shipping restrictions, which provides better RNA separation from liquid samples of biological origin, as well as a method for such separation.

SUMMARY OF THE INVENTION

The present invention relates to an improved method for the separation of RNA from liquid samples of biological origin containing RNA, as well as an improved two-phase liquid composition useful in such a separation. More particularly, the invention calls for a two-phase liquid composition wherein the upper layer is predominately phenol and the lower phase is an aqueous solution containing at least one water-soluble guanidinium salt, a buffer and urea, the composition having controlled phenol and water contents. The invention further calls for the method of separating RNA from liquid samples of biological origin containing RNA, which method employs the two-phase compositions.

DETAILED DESCRIPTION OF THE INVENTION

The present invention includes a two-phase liquid composition wherein the upper phase is predominately phenol and the lower phase is an aqueous solution of at least one water-soluble guanidinium salt, a buffer and urea. Also present in the lower aqueous phase are optional lesser amounts of other components such as surfactants and complexing agents. The two-phase solutions are employed to separate RNA from liquid samples of biological origin containing RNA and other components such as DNA and protein. The separation is more efficient and provides a higher yield of RNA than is obtained by using other, closely related compositions. Subsequent to its separation, the RNA is purified by conventional methods and is useful in biological studies such as gene expression.

The liquid materials to which the process of the invention is usefully applied are the substantially liquid portions of material of animal origin containing RNA, substantially separated from solid or cellular components such as fats, proteins, minerals and hormones. The process of the invention is usefully applied to substantially liquid samples containing small amounts, e.g., less than about 10% by weight, of normally solid components, particularly if the normally solid components are at least partially soluble in the liquid sample. These substantially liquid samples of animal origin are broadly termed "sera" (serum is the singular) and are illustrated by blood serum, lymph, fluids in blisters and fluids in natural cavities of an animal body such as the peritoneal, pleural or pericardial sacs. In a preferred embodiment, the substantially liquid sample of human origin is blood serum, i.e., the liquid portion of blood that remains when blood is allowed to clot spontaneously and the blood cells and clotting elements are removed as by centrifugation. Such sera typically contain from about 6% by weight to about 8% by weight of dissolved solids including proteins.

The compositions used to separate RNA from the substantially liquid solutions containing RNA are two-phase liquid compositions wherein the upper phase is predominately phenol and the lower phase is an aqueous solution containing at least one water-soluble guanidinium salt, a buffer and urea. The presence of two phases is dependent at least in part upon the proportion of phenol present in the total mixture. It is important that the proportion of phenol be such that the two phases exist and proportions of phenol sufficient to maintain two phases are useful. Such proportions are no more than about 40% by weight based on the total mixture. Preferred compositions of the invention contain a proportion of phenol from about 30% by weight to about 38% by weight, inclusive, based on total composition, and especially from about 32% by weight to about 37% by weight, inclusive, based on total composition. The upper phase is predominately phenol in that no more than minor proportions of other materials are present. Trace amounts of materials from the aqueous lower phase may migrate into the phenol, but the phenolic phase is at least about 98% by weight phenol and is preferably at least 99% by weight phenol.

The lower phase of the two-phase compositions of the invention is an aqueous phase containing, in addition to water, at least one water-soluble guanidinium salt, a buffer, urea and lesser amounts of other substances such as surfactants and complexing agents. Illustrative of water-soluble guanidinium salts are guanidinium thiocyanate and guanidinium chloride. The use of at least one of guanidinium thiocyanate and guanidinium chloride is preferred and the use of both these guanidinium salts is particularly preferred in the aqueous phase of the compositions of the invention. The proportion of total guanidinium salt in the composition is suitably from about 15% by weight to about 25% by weight inclusive based on total composition and preferably is from about 17% by weight to about 23% by weight inclusive on the same basis. When both guanidinium thiocyanate and guanidinium chloride are employed, the ratio of one salt to the other is not critical but preferably these salts are utilized in a weight ratio of from about 1:1 to about 3:1.

The urea present in the aqueous phase of the compositions of the invention is present in an amount from about 5% by weight to about 15% by weight inclusive, based on total composition. Preferred quantities of urea are from about 8% by weight to about 11% by weight inclusive on the same basis.

The buffer component of the compositions comprises the salt of a strong inorganic base and a weak organic acid, particularly an alkali metal salt of the weak acid. In preferred buffers the alkali metal moiety is sodium or potassium, particularly sodium, and the weak organic acid is citric acid, tartaric acid or acetic acid. Particularly preferred as buffer is sodium citrate or sodium acetate, especially sodium citrate. The buffer is suitably employed in a quantity of from about 2% by weight to about 7% by weight, based on total composition. The buffer is typically employed in conjunction with a weak organic acid, preferably but not necessarily the organic acid from which the buffer is illustratively formed, e.g., citric acid or acetic acid. The presence of acid is not required and weight amounts of acid up to three times the weight of buffer are useful. Weight ratios of acid to buffer from about 1:4 to about 1:1 inclusive are preferred. The precise pH imparted by the buffer and inorganic acid to the compositions of the invention is not critical, although better results are obtained in the RNA separation process if the apparent pH of the total composition, subsequent to shaking, is from about 3 to about 6, inclusive, particularly about 4.

The presence of additional materials in the aqueous phase of the composition is helpful in obtaining efficient RNA separation but not critical to the practice of the invention. Surfactants and complexing agents are useful and amounts of any such materials which are water soluble of up to about 5% by weight based on total mixture are satisfactory. Sulfate- or Phenol-type surfactants are particularly suitable such as TRITON®-X100, an aromatic phenol surfactant, and sodium lauryl sulfate, an aliphatic sulfate-type surfactant. Useful complexing agents include ethylene diamine tetraacetic acid (EDTA) and nitrilotriacetic acid (NTA). Also useful is the presence of a small amount, e.g., up to about 1% by weight based on total mixture of an antioxidant such as beta-mercaptoethanol. The antioxidant, if present, may be partly soluble in the phenolic phase and serve to stabilize the phenol.

The proportion of water in the composition is of some importance in the compositions designed for RNA separation from liquid samples. In contrast with compositions useful in the separation of RNA from solid samples, the proportion of water in the compositions of the invention is a relatively low quantity of water from about 10% by weight to about 25% by weight, inclusive, based on total composition, are satisfactory. Proportions of water from about 15% by weight to about 23% by weight, inclusive, on the same basis are preferred. Particularly preferred are proportions of water from about 17% by weight to about 20% by weight, inclusive, on the same basis.

The aqueous phase of the composition is substantially free of phenol. Although some minor amount of phenol is soluble in the aqueous phase, any phenol in the aqueous phase comprises no more than about 1% by weight of the aqueous phase.

The compositions are prepared by mixing the components in conventional manner. Good results are obtained if at least the initial mixing of phenol with the other components is conducted at elevated temperature. In a typical preparation, phenol is heated to an elevated temperature, e.g., from about 45° C. to about 70° C., and mixed with at least a portion of the water to be present in the final composition. Other composition components, provided as such or as aqueous solutions, are added to the mixture in no particular order although the addition of guanidinium salt and urea usually occurs before the buffer and minor components are provided.

The resulting composition is two-phase at or about ambient temperature with the upper phase being predominately phenol with at most small amounts of other composition components. The lower phase is an aqueous phase containing guanidinium salt, urea, buffer and any other components. The composition, when shaken, becomes milky with the general appearance of an emulsion. Upon standing, the composition separates into two phases within several minutes.

To effect the separation of RNA from a liquid sample of biological origin, the two-phase composition of the invention is preferably mixed and intimately contacted with the liquid sample. Such contacting is by shaking, agitating or vortexing. The mixing of the composition is preferably conducted before contacting the sample but is alternatively effected during contact with the sample. The RNA is separated by adding to the intimately contacted mixture of sample and composition a relatively dense, water-insoluble solvent, particularly a chlorinated solvent such as chloroform or carbon tetrachloride. The resulting material is a two-phase mixture wherein the RNA of the liquid sample is in the upper aqueous phase. The other biological materials present in the liquid sample such as DNA and protein are in the lower organic phase or at the interface. The aqueous phase is removed to separate the RNA from the other biological components. The RNA is then recovered from the aqueous phase by conventional methods such as evaporation of solvent, selective extraction or absorption.

In practice, however, the RNA, subsequent to recovery, is purified by a series of conventional steps. By one technique, the aqueous phase containing RNA is treated with a lower alkanol such as ethanol or isopropanol in sufficient quantities to precipitate the RNA. The RNA is then recovered by conventional methods such as centrifugation or decantation. In an alternate technique, the aqueous phase is treated with an amount of lower alkanol insufficient to precipitate the RNA and a silica-containing resin is added. A commercially available silica-containing resin, RNA Tack Resin, is satisfactory. The mixture is shaken or otherwise agitated to intimately contact the resin and aqueous solution. The resin, to which the RNA is then bound, is separated as by centrifugation or decantation and any impurities in the RNA are removed as by washing the resin with a solvent selective for the impurities such as ethanol. The RNA is recovered in high purity and in good yield as by eluting the resin with water.

The process of the invention serves to separate RNA is good yield from liquid samples of biological origin. Other methods have been found to be useful in the separation of RNA from relatively solid samples such as tissue or cells, but are inferior to the method of the invention for the separation of RNA from liquid samples.

The RNA obtained by employing the compositions of the invention and the process of the invention is biological material of known utility, being useful, for example, in gene expression.

The invention is further illustrated by the following Illustrative Embodiments which should not be construed as limiting.

ILLUSTRATIVE EMBODIMENT I

One kilogram of crystallized phenol is melted at 60° C. in the presence of 150 ml of distilled water and to the resulting mixture is added 200 ml of sodium citrate buffer at pH 4.0. To this buffered mixture is added 1 liter of 14M aqueous solution of a mixture of guanidinium thiocyanate, guanidinium chloride and urea in weight proportions of 2:1:2. To the resulting two-phase mixture is added 200 ml of 1M aqueous sodium citrate buffer at pH 4, 160 ml of 0.2M aqueous ethylene diamine tetraacetic acid, 50 ml of 10% by weight aqueous sodium lauryl sulfate and 160 ml of Triton-X 100, an alkylated phenolic surfactant. The solution is stabilized with 1 ml of 2-mercaptoethanol which serves as an antioxidant for phenol. The resulting formulation is two-phase wherein the upper phase is predominately phenol. The lower phase is predominately an aqueous solution of the other components. Before use, the mixture is shaken thoroughly and becomes milky.

To prepare a sample for RNA separation from blood, 3–5 ml of blood were collected in a vaccutainer tube. The sample was centrifuged at 2500×g for 20 minutes to separate the serum which was immediately frozen at −70° C. in a sterile RNA-free microfuge tube. Two hundred microliters of this serum were mixed with 1 ml of the shaken reagent as prepared above in a sterile microfuge tube and the mixture was mixed thoroughly by shaking for 30 seconds. To this mixture was added 200 µl of chloroform and the tube was closed and vortexed or shaken by hand for 15 seconds and then maintained at 4° C. for 5 minutes. The mixture was then centrifuged at 12,000 ×g for 15 minutes while maintained at 4° C. The resulting mixture comprised two phases. The lower organic phase and interface contained DNA and proteins and the upper aqueous phase, comprising 40% to 50% by volume of the total mixture, contained RNA.

The upper phase was transferred to a fresh micofuge tube without disturbing the interface. Approximately 400 µl of the aqueous phase was mixed with 200 µl of isopropanol. No precipitation took place. A 20 µl volume of mixed silica resin was added and the mixture was vortexed for 30 seconds. The mixture was then centrifuged for 1 minute to separate the resin, to which the RNA is complexed. The resulting resin pellet was washed twice with 1 ml of 75% ethanol, by vortexing for 30 seconds in each case, to remove impurities. The supernatant liquid from each washing was discarded and after the second washing the RNA was eluted from the resin by mixing with 20 µl of DEPC (diethylpyrocarbonate) treated water. As an alternate procedure, the RNA is eluted by mixing with water and spinning for 30–60 seconds. By either technique, high quality RNA is recovered.

COMPARATIVE EXAMPLES AND ILLUSTRATIVE EMBODIMENT II

In this Illustrative Embodiment, RNA is separated from blood serum employing Ultraspec RNA Isolation System (System 1), Ultraspec-II RNA Isolation System (System 2) and Ultraspec-3 RNA Isolation System (System 3). Systems 1 and 2, not of the invention, have been available commercially since 1992 and 1993 respectively. The liquid portion of each System comprises a two-phase mixture of phenol, water, guanidinium thiocyanate, guanidinium chloride and other components such as are exemplified in Illustrative Embodiment I. Systems 2 and 3 are further characterized by a mixed silica resin, RNA Tack Resin, supplied with the liquid component to facilitate the purification of the RNA subsequent to RNA separation from the serum sample. The liquid components of Systems 1 and 2 are identical and the resin components of Systems 2 and 3 are identical. The composition of the liquid components of the Systems is shown in the following Table 1. The proportions given in grams of chemical per 100 grams of total liquid composition are quite close to percentages by weight for the compositions.

TABLE

| Chemical, g of chemical per 100 ml of liquid composition | Systems 1 or 2 | System 3 |
|---|---|---|
| Phenol | 32.27 | 34.25 |
| Guanidinium Thiocyanate | 9.22 | 13.72 |
| Guanidinium Chloride | 4.61 | 6.84 |
| Urea | 9.22 | 13.72 |

TABLE-continued

| Chemical, g of chemical per 100 ml of liquid composition | Systems 1 or 2 | System 3 |
| --- | --- | --- |
| Sodium Citrate | 3.47 | 4.09 |
| Citric Acid | 2.43 | 2.43 |
| Triton-X 100 | 3.66 | 5.48 |
| Ethylene Diamine Tetracetic Acid | 0.27 | 0.40 |
| Sodium Lauryl Sulfate | 0.11 | 0.17 |
| Beta-Mercaptoethanol | 0.3 | 0.3 |
| Water | 34.71 | 18.60 |

In the System 1 and System 2 methods, 200 μl of blood serum was contacted with 2.0 ml of the mixed extraction reagent and, after contacting, 400 μl of chloroform were added. The resulting mixture, after centrifugation was two-phase mixture wherein the upper aqueous phase contained extracted RNA. The aqueous phase was separated without disturbing the lower phase or interface. In the System 1 method, the RNA was precipitated from the aqueous phase by addition of isopropanol, washed with ethanol and solubilized in DEPC treated water. In the System 2 method, the RNA was purified by mixing the aqueous phase with RNA Tack Resin. The impurities were removed by washing with 75% ethanol and the pure RNA was eluted from the resin with DEPC-treated water.

In the method of the invention, System 3, 200 μl of serum were contacted with 1.0 ml of mixed System 3 reagent and, after contacting, 200 μl of chloroform were added. Two phases were present. The upper aqueous phase was removed and mixed with RNA Tack Resin. Impurities were removed by washing with 75% ethanol and the RNA was eluted from the resin with DEPC-treated water.

From a number of separations by each of the above techniques, the average yield of RNA from the serum by each of the three techniques was determined by spectrometrical examination of the RNA after separation of any contaminants by gel chromatography. The average yields are provided in Table II.

TABLE II

| | Average yield from 100 μl of serum |
| --- | --- |
| Ultraspec-RNA Isolation System | 0.7 μg |
| Ultraspec-II Isolation System | 0.6 μg |
| Ultraspec-3 RNA Isolation System | 3.30 μg |

What is claimed is:

1. In the process of separating RNA from biological samples containing RNA by contacting the sample with a two-phase composition wherein the upper phase is predominately phenol and the lower phase is an aqueous solution containing at least one water-soluble guanidinium salt, a buffer and urea, the improvement which comprises separating RNA from a substantially liquid biological sample with the two-phase composition wherein the phenol is present in a quantity not more than about 40% by weight based on total composition and the water is present in a quantity from about 10% by weight to about 25% by weight, inclusive, based on total composition.

2. The process of claim 1 wherein the substantially liquid sample is blood serum.

3. The process of claim 2 wherein the phenol is present in a quantity from about 30% by weight to about 38% by weight, inclusive, based on total composition.

4. The process of claim 3 wherein the water is present in a quantity from about 15% by weight to about 23% by weight, inclusive, based on total composition.

5. A two-phase liquid composition wherein the upper phase is predominately phenol and the lower phase is an aqueous solution of at least one water-soluble guanidinium salt, a buffer and urea, the phenol is present in a quantity of from about 30% by weight to about 38% by weight, inclusive, based on total composition, and the water of the aqueous phase is present in a quantity from about 10% by weight to about 25% by weight, inclusive, based on total composition.

6. The composition of claim 5 wherein the at least one water-soluble guanidinium salt is at least one of guanidinium thiocyanate and guanidinium chloride in a total amount of from about 15% by weight to about 25% by weight, inclusive, based on total composition.

7. The composition of claim 6 wherein the buffer is an alkali metal salt of a weak organic acid.

8. The composition of claim 7 wherein the alkali metal moiety is sodium and the organic acid is citric acid, acetic acid or tartaric acid.

9. The composition of claim 8 wherein the buffer is sodium citrate.

10. The composition of claim 7 wherein the urea is present in a quantity of from about 5% by weight to about 15% by weight, based on total composition.

11. The composition of claim 10 wherein the predominately phenol phase is at least 98% by weight phenol.

12. The composition of claim 10 wherein the water of the aqueous phase is present in a quantity of from about 15% by weight to about 23% by weight, inclusive, based on total composition.

13. A process of separating RNA from a liquid sample of biological origin containing RNA which comprises intimately contacting the sample with the composition of claim 4, adding to the resulting mixture a water-insoluble solvent thereby forming an aqueous phase containing RNA and an organic phase containing other components of the liquid sample, separating the aqueous phase containing RNA from the remaining mixture, and recovering the RNA from the aqueous phase.

14. The process of claim 13 wherein the liquid sample of biological origin is serum.

15. The process of claim 14 wherein the serum is blood serum.

* * * * *